United States Patent [19]

Slautterback

[11] Patent Number: 5,693,006
[45] Date of Patent: Dec. 2, 1997

[54] METHOD OF USING A LIFTING BELT IN COMBINATION WITH AN ACCESSORY

[75] Inventor: Ernest Gerald Slautterback, Coral Springs, Fla.

[73] Assignee: FLA Orthopedics, Inc., Miami Lakes, Fla.

[21] Appl. No.: 608,700

[22] Filed: Feb. 29, 1996

[51] Int. Cl.$^6$ ............................................. A61F 5/00
[52] U.S. Cl. .................. 602/19; 2/48; 2/51; 224/587; 224/240; 224/901.2; 224/904
[58] Field of Search ................... 602/19; 2/44, 48, 2/51; 224/587, 660, 240, 904, 901.2

[56] References Cited

U.S. PATENT DOCUMENTS

| | | | |
|---|---|---|---|
| 496,816 | 5/1893 | Corker | 602/19 |
| 4,151,938 | 5/1979 | Barker et al. | 2/51 X |
| 4,459,703 | 7/1984 | Kosmas et al. | 2/48 |
| 4,747,527 | 5/1988 | Trumpower, II | 2/311 X |
| 5,148,549 | 9/1992 | Syder | 602/19 X |
| 5,211,163 | 5/1993 | Mortenson | 602/19 X |
| 5,240,156 | 8/1993 | Sicotte et al. | 224/240 X |
| 5,318,507 | 6/1994 | Greengarg | 602/19 |
| 5,385,281 | 1/1995 | Byrd | 2/51 X |
| 5,470,000 | 11/1995 | Muñoz | 602/19 X |

*Primary Examiner*—Linda C. Dvorak
*Attorney, Agent, or Firm*—Jack E. Dominik

[57] ABSTRACT

Disclosed is an accessory base for use with lifting belts. Typically, lifting belts have flaps extending from a lumbar section containing loop fastening material on the exterior sides, and side pulls containing hook fastening material on the interior sides, whereby the hook fastening material on the side pulls can matingly engage the loop fastening material on the exterior sides of the flaps. In effect, the side pulls and flaps utilized according to the present invention for the "sandwiching-type" securement of the accessory base between the side pull and the belt flaps. The accessory base has a hook fastening portion on its inside and a loop fastening portion on its outside to the end that the accessory base can secure itself to the underlying belt flaps, and then be locked in place by the side pulls in sandwich effect. The accessory base has a fold-over cummerbund panel that depends from the upper portion of the accessory base, which panel, after the side pulls are secured, is reversely folded downwardly over the front of the side pulls and masks the flaps and side pulls, while displaying a smart cummerbund facade. The fold-over portion keeps the lifting belt clean by shielding against crumbs, lint, and other debris. The fold-over portion also helps to secure the accessory base to the lifting belt by providing multiple layers of securement.

2 Claims, 4 Drawing Sheets

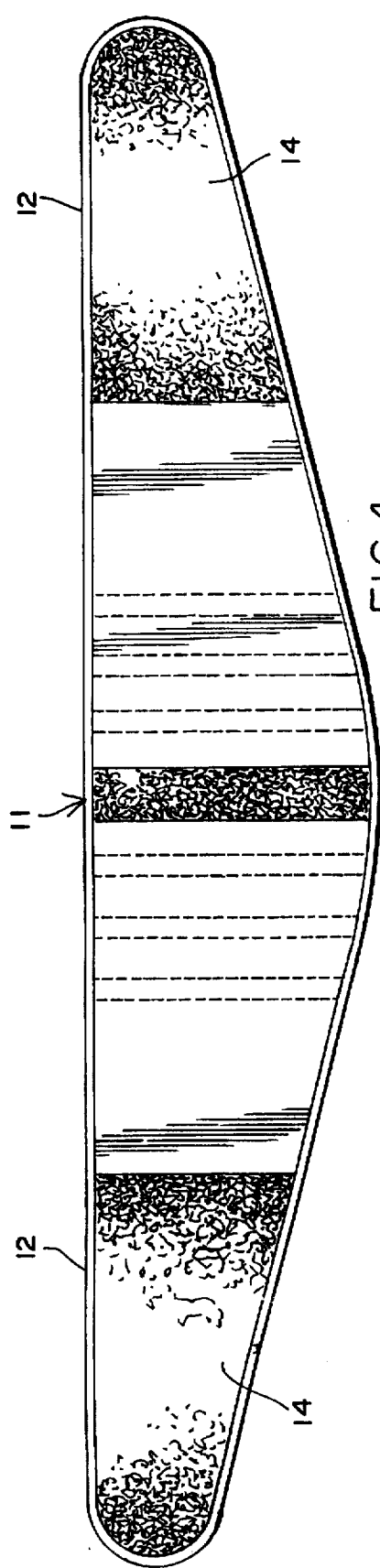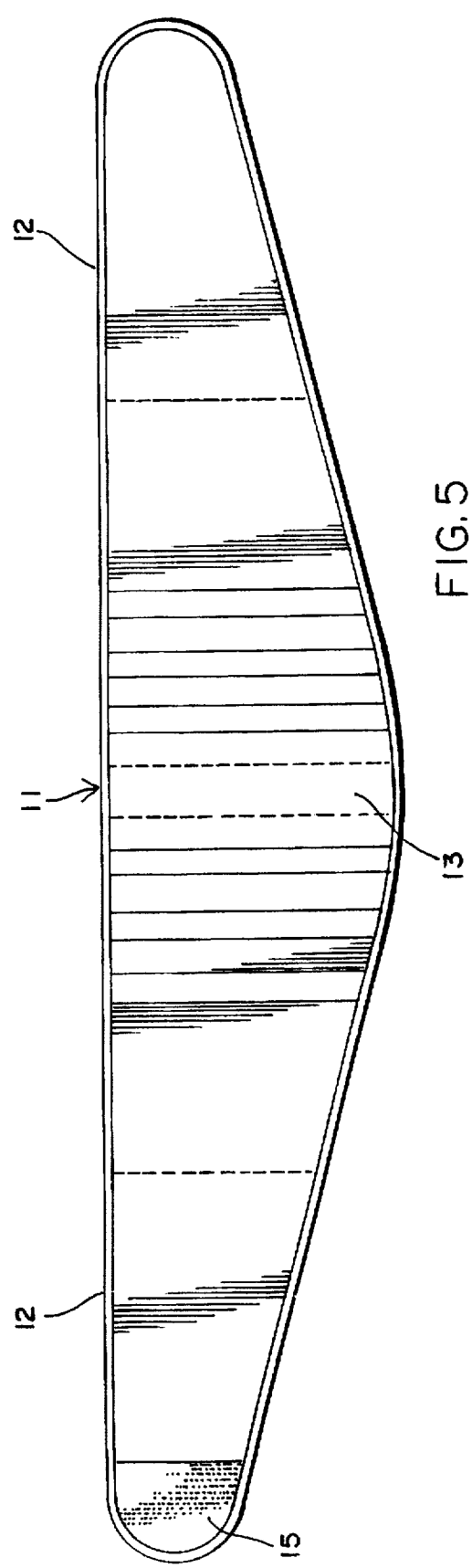
FIG. 4
FIG. 5

METHOD OF USING A LIFTING BELT IN COMBINATION WITH AN ACCESSORY

FIELD OF THE INVENTION

The present invention relates primarily to lifting belt accessories to be worn by waiters, hospital attendants, and other service providers whose work environments require them to present a clean and neat appearance. Lifting belts are worn to inhibit awkward positions and the attendant back injuries that result from improper lifting, but because of their appearance and their association with more industrial environments, lifting belts are often under-utilized.

SUMMARY OF THE PRIOR ART

A wide variety of lifting belts have been developed to address the problem of back injuries caused by improper lifting. Exemplary of such belts are U.S. Pat. Nos. 5,147,261 issued Sep. 15, 1992; 5,399,151 issued Mar. 21, 1995; 5,318,507 issued Jun. 7, 1994; and 5,148,549 issued Sep. 22, 1992. Some of these belts have included aprons either as a unitary portion or separately secured. Aprons in many instances raise problems because they are secured around the neck by a loop. In the event the wearer should have any portion of the apron caught in machinery or other moving items, injury could result. Also another aspect of the prior-art lifting belts is their lack of aesthetic attractiveness, which is highly undesirable in many environments, including for example, settings such as hospitals, restaurants and bars. For a waiter or waitress in a restaurant, a sleek looking appearance around the waist is desirable, but in some instances, a depending skirt having pockets to hold order pads, crumb scoops, pencils and pens, matches, and related paraphernalia is also desirable.

SUMMARY OF THE INVENTION

The present invention stems from the fact that most of today's lifting belts utilize hook and loop or equivalent removable fastening material to allow for easy adjustment of the outer and inner belts. Typically, lifting belts have flaps extending from a lumbar section containing loop fastening material on the exterior sides, and side pulls containing hook fastening material on the interior sides, whereby the hook fastening material on the side pulls can matingly engage the loop fastening material on the exterior sides of the flaps. In effect, there is an overlapping relationship between the side pulls and flaps which is utilized according to the present invention for the "sandwiching-type" securement of an accessory base between the side pull and the belt flaps. The accessory base has a hook fastening portion on its inside and a loop fastening portion on its outside to the end that the accessory base can secure itself to the underlying belt flaps, and then be locked in place by the side pulls in sandwich effect. The accessory base has a fold-over cummerbund panel that depends from the upper portion of the accessory base, which panel, after the side pulls are secured, is reversely folded downwardly over the front of the side pulls and masks the flaps and side pulls, while displaying a smart cummerbund facade. The fold-over portion also serves two other functions. It keeps the loop fastening material on the exterior of the flap clean by shielding against crumbs, lint, and other debris. The fold-over portion also helps to secure the accessory base to the lifting belt by providing multiple layers of securement. The accessory base is secured by the sandwiching between the side pulls and the flaps, as well as secured by the reversely folded cummerbund panel that covers the overlapping flaps and side pulls. It takes considerably more force to disengage an accessory base with an overlapping cummerbund than one without an overlapping member. Therefore, the present invention can be used to store many items without fear of dislodging the accessory base.

The accessory base is normally of a width sufficient to cover the entirety of the underlying belt flaps and side pulls. In an alternative embodiment, the reversely folded cummerbund portion has a depending half apron with pockets and straps to allow the user to handily store the desirable tools of the trade.

It is contemplated that the relative positioning of the hook fastening material and the loop fastening material of the accessory base may need to be reversed depending upon the fastening material that is located on the overlapping belt flaps and the side pulls. Obviously, the fastening material on the accessory base is selected to matingly engage the materials of the lifting belt.

In view of the foregoing it is a primary object of the present invention to provide an accessory base for use with a lifting belt which is installed between the side pulls and the underlying belt flaps and to allow the wearer to take advantage of the sandwich effect of the belt flaps and the side pulls to sandwich the accessory base in between the belt flaps and the side pulls. This results in a very snug positioning of the accessory base resisting dislodging, and at the same time presenting a neat and uncluttered exterior appearance.

Another object of the present invention is to provide an aesthetically pleasing, practical facade for a lifting belt that allows the wearer to wear a lifting belt in work environments where an unsightly lifting belt would otherwise be prohibited.

Yet another object of the present invention is to provide a aesthetically pleasing cover to shield the underlying material against soiling. Without the cover, the belt is prone to collecting lint, dirt and other debris.

Yet another object of the present invention is to provide an accessory base to the lifting belt which requires no modifications to the lifting belt and side pull other than proportioning for certain applications. This restricts the cost of the accessory base to its own inherent cost, and not a cost escalated by the necessity of a modification of the underlying lifting belt.

As a corollary to the foregoing object, it is further an object of the present invention to provide an accessory base to a lifting belt which is adaptable to a wide variety of lifting belt constructions such as exemplified by the United States patents set forth in the Summary of the Prior Art section set forth above.

BRIEF DESCRIPTION OF THE DRAWINGS

Further objects and advantages of the present invention will become apparent from the following description of several illustrative embodiments, taken in conjunction with the accompanying drawings, in which:

FIG. 4 is a front planar view of the exterior of the belt member of the lifting belt assembly;

FIG. 5 is a front planar view of the interior of the belt member of the lifting belt assembly;

FIG. 8 is a perspective view that shows how the belt members of the lifting belt assembly can be secured each to the other and also shows the fastening material on the interior of the accessory base.

FIG. 9 illustrates how the accessory base can be secured to the overlapping belt members by engaging the fastening material on the exterior of the accessory base with the fastening material on the overlapped belt members.

FIG. 10 illustrates how the side pulls of the lifting belt assembly are secured to the fastening material on the exterior side of the accessory base, hence, sandwiching the accessory panel between the overlapped belt members and the side pulls.

FIG. 11 illustrates how the cummerbund panel of the accessory base can be folded downward to cover the fastening material and the side pulls secured thereto.

DESCRIPTION OF A PREFERRED EMBODIMENT

Figure 1:
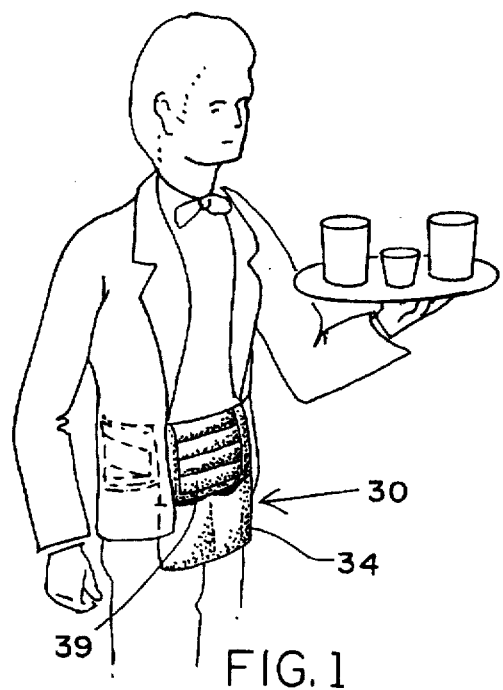
FIG. 1 shows a waiter dressed semi-formally with a black jacket, black tie, white shirt, carrying a tray of meals, and wearing a lifting belt which utilizes the cummerbund decorative accessory center piece.

FIG. 1 illustrates a waiter 1 utilizing one of the preferred embodiments of a lifting belt assembly 10 using an accessory base 30. Reference numerals 10 and 30 refers to the lifting belt assembly and the accessory base in their entireties, respectively. From the front, only the cummerbund 39 and the apron-like section 34 can be seen because the cummerbund 39 hides the overlapping belt flaps 12 and the side pulls 21.

Figure 2:
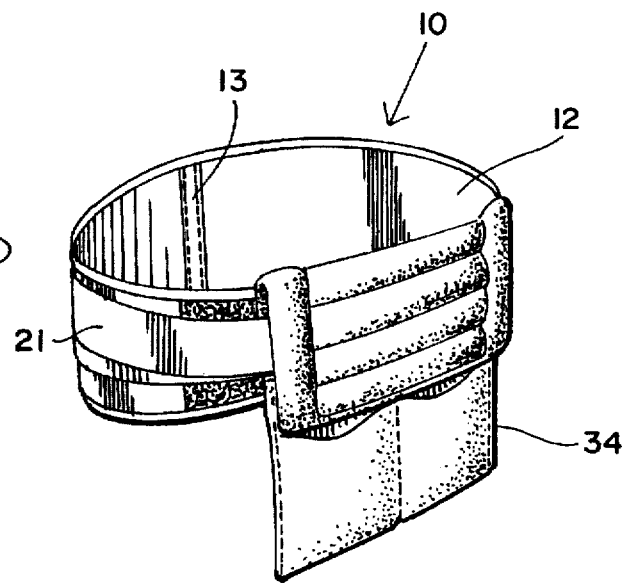
FIG. 2 is an enlarged focussed view of the same belt shown in FIG. 1, but illustrating the cummerbund along with a downwardly depending apron, which apron requires no securement other than its removable securement to the lifting belt itself.
Figure 3:
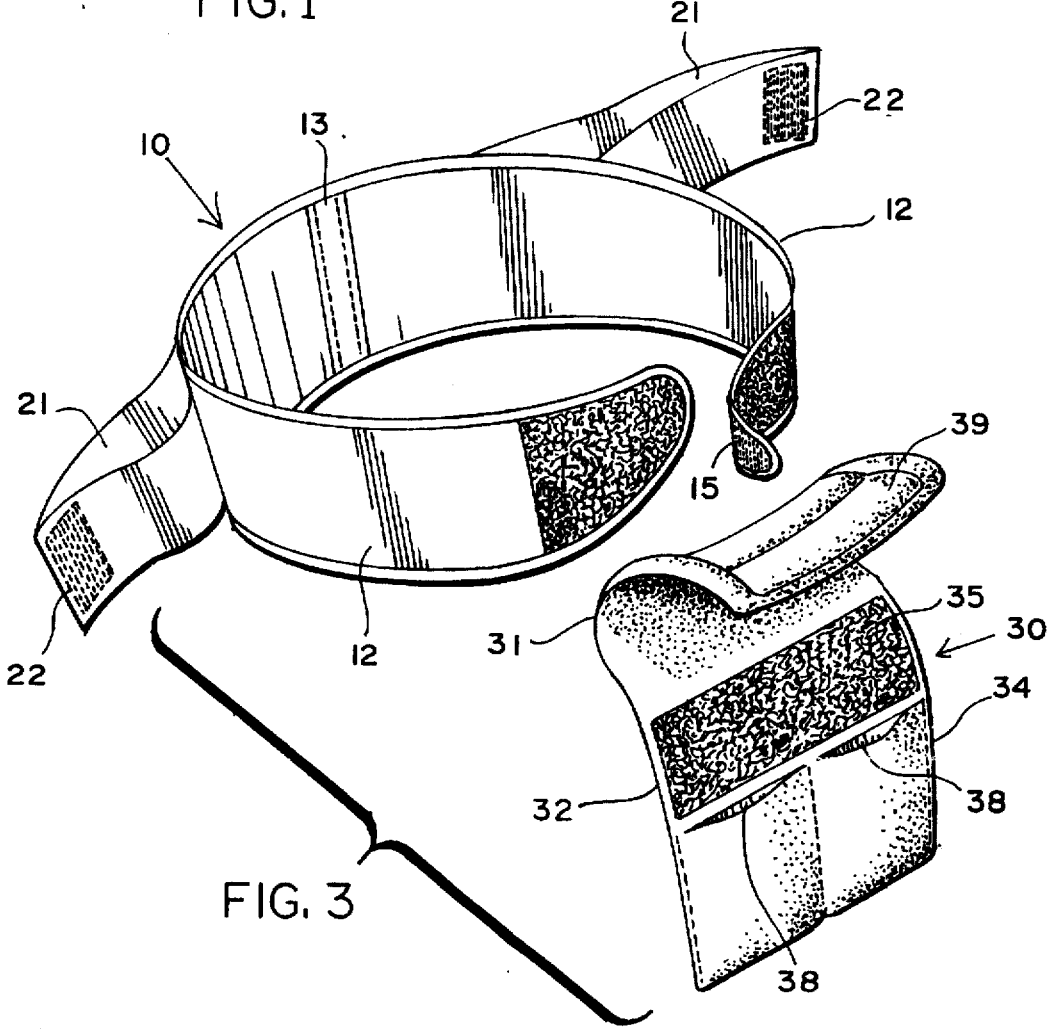
FIG. 3 is a perspective view of a lifting belt assembly and the accessory base showing the primary components of the lifting belt.
Figure 6:
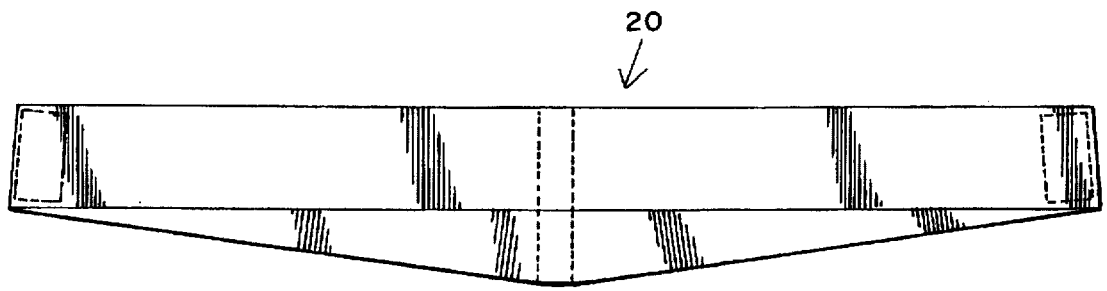
FIG. 6 is a front planar view of the exterior of the elastic side pull member of the lifting belt assembly.
Figure 7:
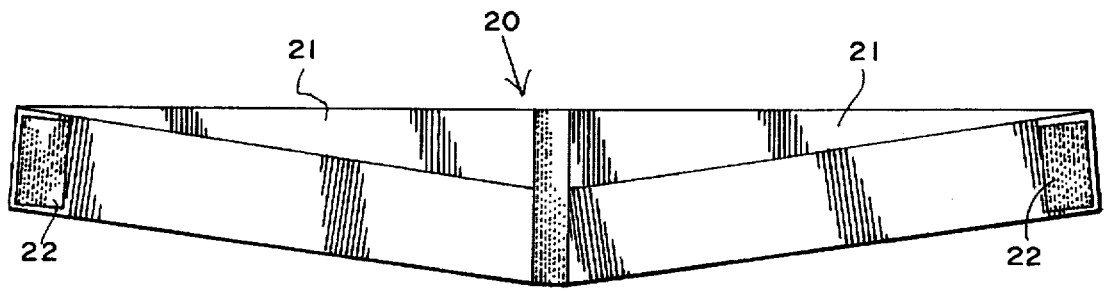
FIG. 7 is a front planar view of the interior of the elastic side pull member of the lifting belt assembly.
Figure 8:
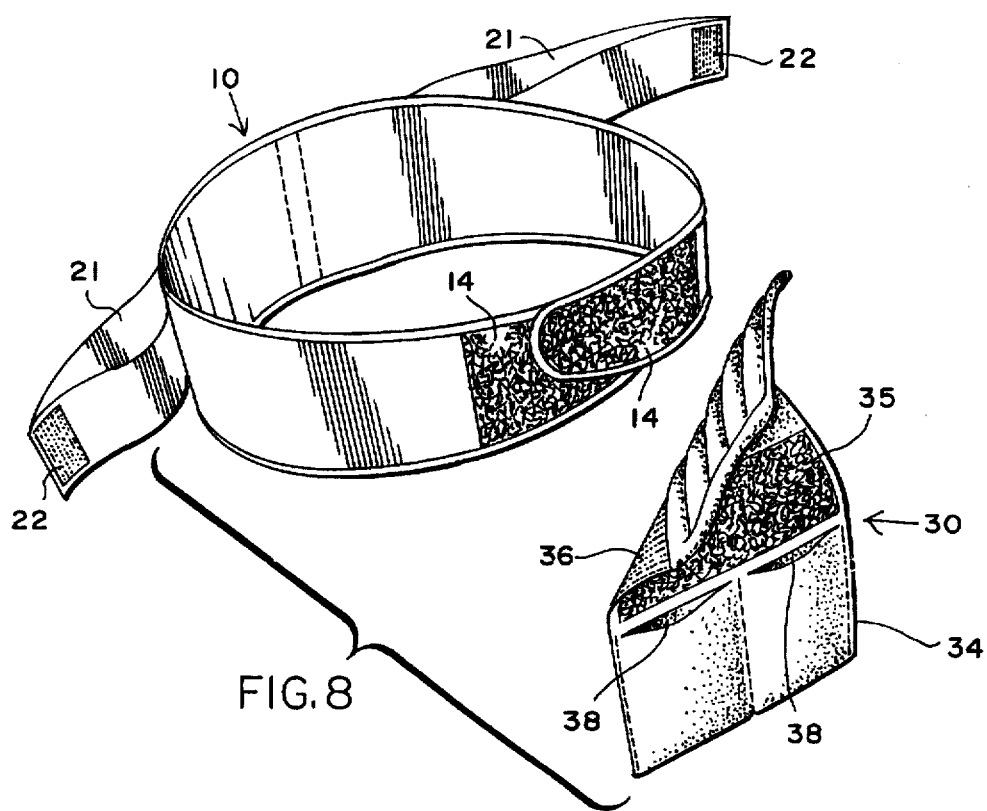
FIGS. 8–11 demonstrate the method of the present invention.
Figure 9:
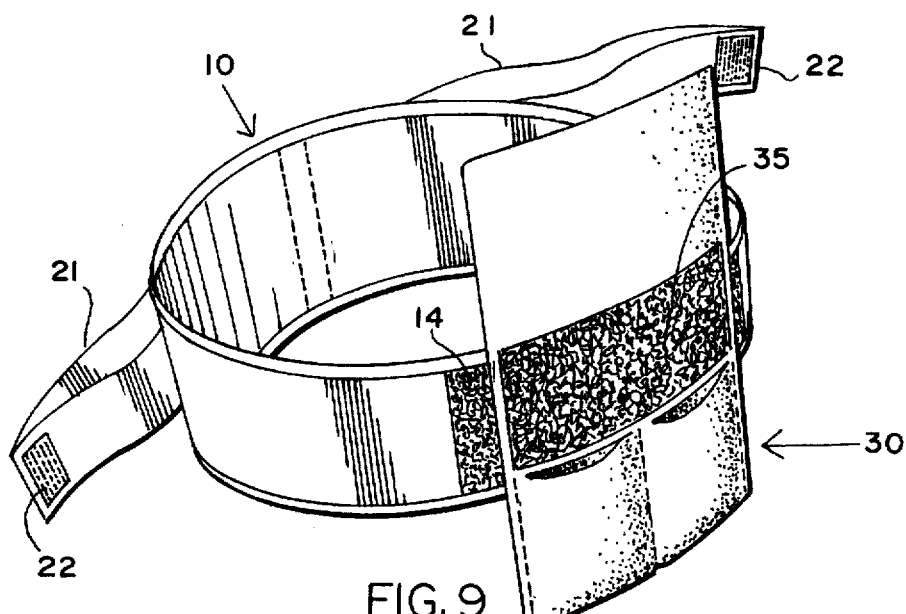
Figure 10:
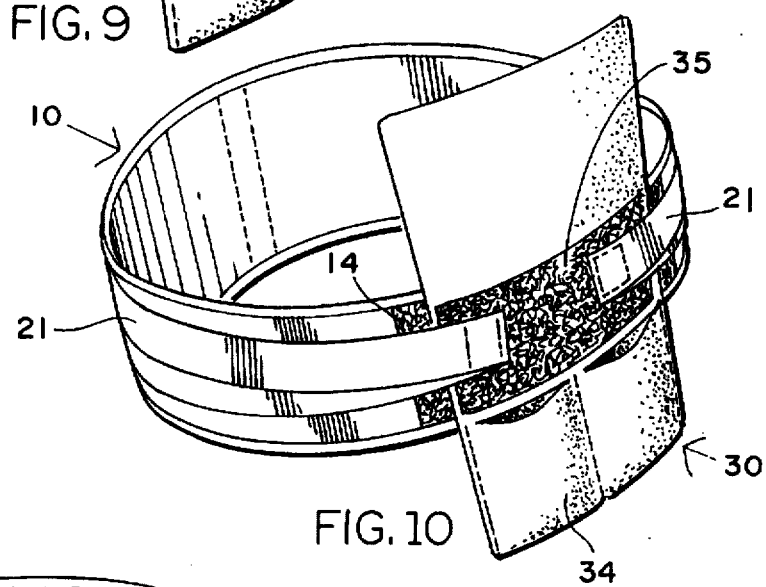
Figure 11:
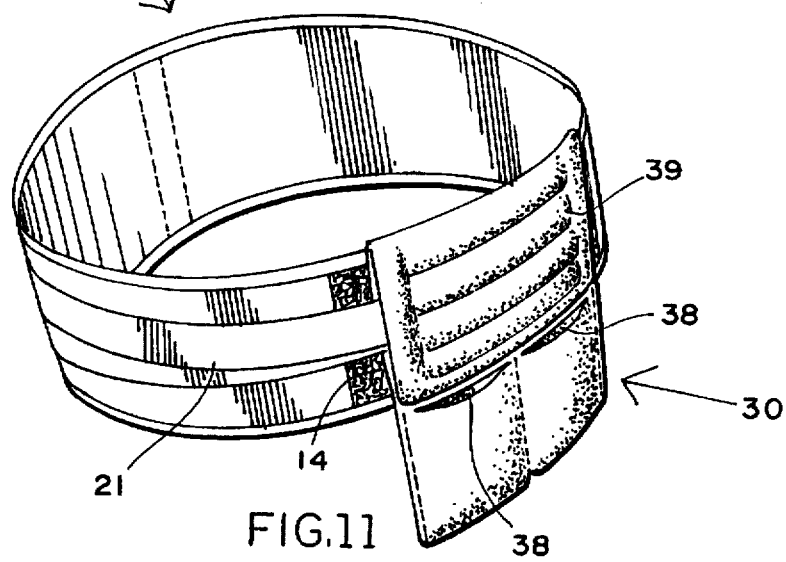

In FIG. 2 the belt flaps 12, the side pulls 21, and the lumbar panel 13 are shown. FIGS. 4 and 5 show the belt member 11, while FIGS. 6 and 7 show the elastic sidepull member 20. In FIGS. 8–11, the lifting belt assembly 10 is displayed showing how the various components may be wrapped around a person and how the accessory base 30 may be removably sandwiched between the overlapped belt flaps 12 and the side pulls 21.

The accessory base 30 is designed to be used with existing lifting belt assemblies 10 without requiring any additional parts for securement. The accessory base 30 is securely sandwiched between the overlapping belt flaps 12 and the side pulls 21 and will not slip or slide about because of the interaction between the fastening panels 36 with the belt flaps 12 and the loop fastening strip 35 with the side pulls 21. Furthermore, the folding member 31 completely covers the sandwiching effect of the aforementioned components to present a neat and tidy appearance. Once in place, the folding member 31 serves several purposes: keeping the loop fastening material 14 clean; presenting a clean, neat, and professional appearance by hiding the unsightly appearance of the lifting belt assembly 10; increasing the degree to which the accessory base 30 is secured to the lifting belt assembly 10. It takes greater force to remove a sandwiched, over-lapped accessory base than it does to remove a sandwiched, non-overlapped accessory base, and therefore, the wearers of the lifting belts can have greater confidence that their fully-loaded accessory bases will not become weighted down to the point that the accessory base is dislocated. Furthermore, the present invention avoids the use of neck loops which can pose significant dangers in some environments. The sandwiching technique of the present invention provides a stable and secure accessory base and therefore, does not need neck loops for additional support.

if the user works in a service industry where appearance is very important, for example in a restaurant, the folding member 31 of the accessory base 30 may be designed to present a cummerbund 39 once the folding member 31 is folded downwardly. Additionally, the apron-like section 34 of the accessory base 30 may be customized for the individual user. For example, a waiter or waitress may require the use of pockets 38 to hold order forms and other tools. In an alternative embodiment, the accessory panel 30 could include stretch bands for holding elongated tools, for example, a crumb scoop.

The method of attaching the accessory base 30 to the lifting belt assembly 10 is described as follows. The wearer places the lumbar panel 13 adjacent his or her back and secures the belt member 11 around himself or herself by removably securing the belt flaps 12 one to the other. This is achieved by engaging the hook fastening material 15 on one of the belt flaps 12 into the loop fastening material 14 of the other belt flap 12. Once secured, the overlapping flaps 12 present a frontal surface comprised of loop fastening material 14. Then, the wearer secures the accessory base 30 by engaging the fastening panels 36 on the interior surface of the middle section 32 with the loop fastening material 14 on the exterior surface of the overlapping belt flaps 12. Thereafter, the wearer adjusts and secures the elastic sidepull member 20 to the exterior surface of the lumbar panel 13. Then, the wearer adjusts and secures the elastic sidepulls 21 to the loop fastening strip 35 located on the exterior surface of the middle section 32 of the accessory base 30 by engaging the hook fastening material 22 on the sidepulls 21 with the loop fastening strip 35. Finally, the wearer folds downwardly the folding member 31 of the accessory base 30 to cover the overlapping belt flaps 12 and the side pulls 21, thus, presenting a neat and tidy appearance for the wearer of the accessory base 30.

Although particular embodiments of the invention have been shown and described in full here, there is no intention to thereby limit the invention to the details of such embodiments. On the contrary, the intention is to cover all modifications, alternatives, embodiments, usages and equivalents that fall within the spirit and scope of the present invention, specification and appended claims. For example, while the primary releasable securable means for the accessory base is of the type that utilizes hook-fastening and loop-fastening materials that matingly engage each other, other types of functionally equivalent means are contemplated by the present invention. Moreover, the relative positions of hook-fastening and loop-fastening material can be readily swapped, and therefore, there is no intent to limit the invention based upon the relative positions of said releasable securable materials. It is intended that an equivalent base and belt are created by swapping the relative positions of the hook fastening and loop fastening materials on both the accessory base and the lifting belt to which the base is attached.

What is claimed is:

1. A method for attaching accessory bases to a lifting belt having overlapping belt flaps and side pulls, said belt flaps and side pulls having interior and exterior sides, said belt flaps being removably securable each to the other and having loop fastening material on their exterior surfaces, said side pulls having hook fastening material on their interior surfaces, whereby the side pulls can be removably secured to the overlapped belt flaps by engaging the hook fastening material of the side pulls with the loop fastening material of the belt flaps, said method comprising in combination the following steps:

- placing the lifting belt on a wearer by wrapping the belt flaps around the waistline of the wearer and removably securing the belt flaps to each other;
- removably securing an accessory base having a middle section with a fastening panel of hook fastening material on the interior surface of said accessory base by engaging the hook fastening material of the accessory base with the loop fastening material on the exterior surfaces of the belt flaps, said accessory base further having a fastening strip on the reverse exterior surface opposite the fastening panel, said accessory base further having a reversely foldable member that extends upwardly from the middle section that can be folded downwardly;
- removably securing the side pulls to the fastening strip of the accessory base by engaging the hook fastening material of the side pulls with the loop fastening material of the fastening strip; and
- folding down the reversely foldable member of the accessory base to cover the overlapping belt flaps and side pulls, thereby removably securing the accessory base by sandwiching said base between the overlapped belt flaps and the side pulls.

2. A method for attaching accessory bases to a lifting belt having overlapping belt flaps and side pulls, said belt flaps and side pulls having interior and exterior sides, said belt flaps being removably securable each to the other and having releasable fastening material on their exterior surfaces, said side pulls having releasable fastening material on their interior surfaces, whereby the side pulls can be removably secured to the overlapped belt flaps by engaging the releasable fastening material of the side pulls with the releasable fastening material of the belt flaps, said method comprising in combination the following steps:

- placing the lifting belt on a wearer by wrapping the belt flaps around the waistline of the wearer and removably securing the belt flaps to each other;
- removably securing an accessory base having a middle section with a fastening panel of releasable fastening material on the interior surface of said accessory base by engaging the releasable fastening material of the accessory base with the releasable fastening material on the exterior surfaces of the belt flaps, said accessory base further having a fastening strip on the reverse exterior surface opposite the fastening panel, said accessory base further having a reversely foldable member that extends upwardly from the middle section that can be folded downwardly;
- removably securing the side pulls to the fastening strip of the accessory base by engaging the releasable fastening material of the side pulls with the releasable fastening material of the fastening strip; and
- folding down the reversely foldable member of the accessory base to cover the overlapping belt flaps and side pulls, thereby removably securing the accessory base by sandwiching said base between the overlapped belt flaps and the side pulls.

* * * * *